United States Patent [19]

Kelman et al.

[11] Patent Number: 5,067,961
[45] Date of Patent: Nov. 26, 1991

[54] NON-BIODEGRADABLE TWO PHASE CORNEAL IMPLANT AND METHOD FOR PREPARING SAME

[75] Inventors: Charles D. Kelman, New York, N.Y.; Dale P. DeVore, Chelmsford, Mass.

[73] Assignee: Autogenesis Technologies, Inc., Acton, Mass.

[21] Appl. No.: 481,503

[22] Filed: Feb. 15, 1990

Related U.S. Application Data

[63] Continuation-in-part of Ser. No. 157,638, Feb. 18, 1999, Pat. No. 4,969,912.

[51] Int. Cl.⁵ .................................................. A61F 2/14
[52] U.S. Cl. .............................................. 623/5; 623/4
[58] Field of Search ............................... 623/4, 5, 66

[56] References Cited

U.S. PATENT DOCUMENTS

4,268,131  5/1981  Miyata et al. ............... 351/160 H

Primary Examiner—David J. Isabella
Assistant Examiner—Debra S. Brittingham
Attorney, Agent, or Firm—Darby & Darby

[57] ABSTRACT

The present invention provides a non-biodegradable corneal implant comprising (1) a polymerized transparent collagenous core having acylated amine or esterified carboxyl groups, and (2) a polymerized periphery surrounding the core, the periphery comprising fibrous collagen, e.g., Type I, being in the form of fibrils under suitable physiological conditions, or fibrillar collagenous material prepared from intact tissue. A method of preparing such an implant is also provided.

27 Claims, 2 Drawing Sheets

NON-BIODEGRADABLE TWO PHASE CORNEAL IMPLANT AND METHOD FOR PREPARING SAME

This is a continuation-in-part application of U.S. Patent Application Ser. No. 157,638, filed Feb. 18, 1988, now U.S. Pat. No. 4,969,912, issued Nov. 13, 1990, the contents of which are hereby incorporated by reference.

FIELD AND BACKGROUND OF THE INVENTION

The present invention relates to a non-biodegradable corneal implant and a method of preparing such an implant. More particularly, this invention relates to a non-biodegradable corneal implant comprising (1) a polymerized soluble transparent collagenous core having acylated amine groups or esterified carboxyl groups, and (2) a polymerized opaque periphery surrounding said core, said periphery comprising polymerized fibrous collagen, said collagen being in the form of fibrils under suitable physiological conditions. The corneal implant is useful in human corneal transplantation, for example, replacement of damaged cornea, corneal inlays or corneal onlays.

Much of the contents of U.S. Pat. No. 4,969,912 has been published. See, e.g., European Patent Application Publication No. 330,389, published Aug. 30, 1989.

Various materials have been described for use as transplantable corneal implants.

In U.S. Pat. Nos. 4,505,855 and 4,581,030 Bruns et al. disclose native, non-fibrilized transparent collagen material that can be fixed, i.e., cross-linked to form a prosthetic cornea replacement. The collagen material employed by Bruns et al. is soluble or rendered soluble by treatment with dilute acids, e.g., acetic acid; base, e.g., NaOH; and in dilute aqueous salts, e.g., NaCl. Bruns et al.'s pelleted collagen material is described as exhibiting strand like structures upon electron microscopic examination (see U.S. Pat. No. 4,505,855 and U.S. Pat. No. 4,581,030, col. 6, Example 3). However, the materials and corneal prosthesis disclosed in the Bruns et al. patents are not suitable for promoting cell ingrowth and enhancing the adhesion of the prosthesis to surrounding recipient tissue after transplantation.

In U.S. Pat. No. 4,772,283, White discloses a corneal implant prosthesis having a transparent lenticula to which is attached a carrier that is constructed from preserved biological tissue, e.g., cornea, sclera, fascia. The transparent lenticula can be made from a number of "non-biological materials", such as polymethylmethacrylate (PMMA), polycarbonates, polyhydroxyethylmethacrylate (HEMA), polysulfones and silicones. White's implant prosthesis is difficult to construct, however, because in order to attach such "non-biological" materials to the carrier, it is necessary to carry out elaborate and time consuming mechanical procedures, such as driving states into place where the lenticula and carrier are to be joined and heat fusing the tissue. Alternatively, the carrier tissue may be retained in the peripheral groove of the lenticula by crimping flanges which have been provided on the latter.

In U.S. Ser. No. 157,638 and European Patent Application Publication No. 330,389, there is disclosed a chemically modified, crosslinkable, solubilized collagenous substance obtained from autogenic intact human tissue, i.e., the donor and recipient are the same individual. This collagenous substance is useful as a corneal implant among others.

It would be highly desirable, therefore, to discover a corneal implant which would overcome the disadvantages of prior art materials, prosthesis, implants, and the like, such as the aforementioned construction problem and the difficulty in incorporating the implant into neighboring endogenous tissue of the recipient following transplantation.

OBJECTS OF THE INVENTION

It is among the objects of the present invention to prepare a non-biodegradable corneal implant that is easily incorporated into endogenous recipient tissue following transplantation without adverse immunologic reaction.

These and other objects of the present invention will be apparent to those skilled in the art, in light of the accompanying description, drawings and appended claims.

SUMMARY OF THE INVENTION

The present inventor has discovered that a non-biodegradable two-phase corneal implant can be prepared using different but compatible collagenous materials as the lens core and as the peripheral opaque carrier or attachment portion. The core comprises a polymerized soluble transparent collagenous core having acylated amine groups or esterified carboxyl groups. The opaque periphery surrounding the core comprises fibrous polymerized collagen, said collagen being in the form of fibrils under suitable physiological conditions so as to attach to endogenous tissue following transplantation of the implant into a subject recipient.

The present inventor has discovered that the just-described non-biodegradable corneal implant can be prepared by following the steps of either incubating neutralized acid soluble collagen under conditions sufficient so that the collagen forms fibrils and then recovering the collagen fibrils that are formed, or preparing collagen fibrils from intact dermis by treating dermis with acylating or esterifying agents and recovering the fibrous fraction by centrifugation. The fibrous fraction is then suspended in sterile water and added to physiological solution to form fibrils which are subsequently recovered by centrifugation. The recovered collagen fibrils are treated or contacted with a binding agent to bind the fibrils followed by a polymerizing or cross-linking step. At this point, a core of the polymerized (cross-linked) collagen fibrils is excised (cut out) and replaced with a soluble collagen material that is next subjected to polymerizing conditions to cross-link the core material and thereby yield a non-biodegradable corneal implant suitable for human corneal transplantation and other corrective ophthalmic procedures. A preferable alternate procedure involves forming the fibrous ring around a clear central core of soluble collagen and then polymerizing or crosslinking the two phase lens as one unit.

BRIEF DESCRIPTION OF THE FIGURES

FIG. 1 represents three embodiments of the two phase corneal implants of the present invention.

FIG. 2 illustrates a non-limiting range of dimensions of the two phase corneal implant.

DETAILED DESCRIPTION OF THE INVENTION

All literature references, patents and patent publications cited in this specification are hereby incorporated by reference in their entirety.

The present invention provides a non-biodegradable corneal implant comprising: (1) a polymerized transparent core, (lenticula), which comprises a polymerized soluble transparent collagenous core having acylated amine groups or esterified carboxyl groups, and (2) a polymerized opaque periphery surrounding said core, the periphery comprising fibrous collagen in the form of fibrils under suitable physiological conditions.

In order to minimize the risk of graft rejection and other adverse immunologic reactions, it is preferred that the tissue from which the implant core and periphery are constructed, be autogeneic, i.e., obtained from the individual recipient. This is particularly the case with the material used to construct the periphery of the implant.

In the case of the collagenous core, this component can be prepared from autogeneic Type I collagen (i.e., obtained from the individual recipient) or from Type IV collagen (e.g., human umbilical tissue). The transplant core may alternately be composed of known synthetic polymers such as PMMA, HEMA, sulfones, etc. In preferred embodiments of this invention, the collagenous core is derived from at least one member selected from the group consisting of purified Type I collagen, purified Type IV collagen, predominantly Type I collagenous preparation obtained from human tissue, e.g., dermis. Preferably the core (1) comprises a Type I collagenous preparation or material obtained from human tissue. As used herein, the purity of the Type I collagen or Type IV collagen comprises from about 70 to about 100 weight percent, preferably from about 95 to about 100 weight percent. In a further preferred embodiment, the predominantly Type I collagenous material comprises fibril forming collagen, the preparation of which is described in detail below and in the examples which follow. As used herein, the term "predominantly" refers to a high concentration of Type I collagen in the collagenous preparation, e.g., from about 70 about to 95 weight percent, preferably from about 80 to about 95 weight percent.

Methods for preparing the soluble collagenous core material having acylated amine or esterified carboxyl groups are described in the aforementioned U.S. Pat. No. 4,969,912 and European Patent Application Publication No. 330,389.

These methods entail the following procedures. Attendant noncollagenous protein contaminates including lipid constituents are desirably removed from telopeptide (non-helical extension peptides) collagen-containing intact autogenic tissue, i.e., tissue that has been obtained from a sole human donor, to form essentially purified telopeptide collagen-containing tissue material, and extracting and chemically modifying the purified telopeptide collagen to form an autoimplantable, crosslinkable substance useful as the periphery material in the present invention.

The contaminates may be removed by contacting the tissue with a substantially neutral liquid which is capable of solubilizing contaminates without solubilizing the collagen, or by utilizing specific enzymes to solubilize noncollagen tissue components.

At this stage in the processing, a fibrous collagenous matrix has been prepared which is capable of forming fibrils under suitable physiological conditions and is therefore, useful as the periphery of the corneal implant of this invention. This human fibril forming collagen (human FF collagen) is not soluble in organic acids as is bovine FF collagen. Human FF collagen is dispersed by chemical treatment into a form that will undergo rapid fibril organization when mixed or contacted with physiological fluid. As used herein, "suitable physiological conditions" include neutral pH, e.g. 6.8, human body temperature and the presence of buffer, e.g., phosphate buffer.

When contacted in this way, i.e., phosphate buffer, pH 6.8 and approximately 37° C. temperature, fibril formation of the human FF collagen from suspensions in water will begin to occur in about 30 minutes.

In order to obtain the collagenous core material, the contaminate-free telopeptide collagen is then extracted by reaction of the tissue directly with a chemical modifying agent, e.g., acylating agent or esterifying agent.

The acylating agent is amine reactive. The acylation reaction is carried out in a solubilizing aqueous medium of substantially neutral to basic pH sufficiently to solubilize at least partially the telopeptide collagen in the aqueous medium, with the at least partially solubilized collagen thereafter being recovered and purified to form the autoimplantable telopeptide-containing collagenous substance as product.

The esterifying agent is carboxylic acid reactive, and in this instance, the esterifying reaction is carried out in a solubilizing nonaqueous organic medium at acidic pH sufficiently to solubilize at least partially the telopeptide collagen therein, with the at least partially solubilized collagen thereafter being recovered and purified to form the autoimplantable telopeptide-containing collagenous core substance as product. It should be understood that while both acylation and esterification of the collagen can be carried out in accordance with the present invention, the yield of clear, transparent modified collagen from the esterification of soluble, mammalian, e.g., bovine, collagen is generally less than that obtained by acylation. Alternatively, the chemical modification may be carried out using both the amine acylating and carboxylic acid esterifying steps.

For the amine modifying reaction, the noncollagenous protein contaminate-free, and lipid-free extracted, tissue powder is resuspended in aqueous medium. The suspension may be in any appropriate aqueous medium such as water, deionized water, balanced salt solution, saline solution, etc., preferably 0.05 to 0.5 M buffer at pH 9.0, i.e., Tris buffer, bicarbonate, etc.

Although the amine modifying reaction will proceed at a pH of from about 7 to about 11, it is preferably effected at mildly basic pH to increase the reaction speed and reduce the processing time. The reaction is desirably effected at about pH 8.0–10.0, and especially at about pH 8.5–9.0.

The amine reactive modifying agent used as a solubilizing agent may be an acylating agent, such as a carboxylic acid anhydride, e.g., succinic anhydride, glutaric anhydride, benzoic anhydride, 1,2,4,5-benzene tetracarboxylic acid dianhydride; carboxylic acid ester, e.g., monophenyl terephthalate, ethyl benzoate, alpha-naphthoic acid ethyl ester; carboxylic acid halide, e.g., succinic acid chloride; sulfonic acid, e.g., 1,3-benzenedisulfonic acid, aniline-2-sulfonic acid, 3-nitro-benzenesulfonic acid, 2-formylbenzene-sulfonic acid, 4-aminonaphthalene-sulfonic acid; or sulfonic acid halide, e.g., 4,4'-biphenyl-disulfonyl chloride, benzene sulfonyl chloride; and mixtures thereof. Preferred as the acylating agent is glutaric anhydride, and combinations of glutaric anhydride with methacrylic anhydride, ethylene/maleic anhydride; B-sulfonyl chloride.

In general, the acylating agent may be an aliphatic or aromatic, mono-, di- or higher functional, carboxylic acid anhydride, ester or halide, or sulfonic acid or halide, such as a lower alkanoic, lower alkane-dioic or higher functional lower alkane carboxylic, or aryl mono-, di- or higher functional carboxylic (e.g., benzoic or naphthoic), acid anhydride, ester or halide, or lower alkyl, or aryl (e.g., phenyl or naphthyl), mono-, di- or higher functional sulfonic acid or halide, to provide the corresponding acyl (carbonyl or sulfonyl) moiety on the amine group, e.g., lower alkanoyl, aroyl (e.g., phenoyl or naphthoyl), alkyl sulfonyl, or aryl (e.g., phenyl or naphthyl) sulfonyl, substituted amino (amido or sulfonamido).

The acylating agent may be added directly as a solid material, e.g., powder, or dissolved in a suitable organic solvent such as acetone, N,N-dimethylformamide (DMF), ethanol, or methyl pyrrolidone.

The total quantity of acylating agent added depends on the extent of disruption, modifying and extracting of the telopeptide collagen desired. For instance, one addition at 150 mg agent per gram of wet tissue may not be sufficient to disperse and solubilize totally the collagen content of the tissue; as many as four such additions may be required.

The quantity required should generally satisfy the weight ratio of acylating agent to wet tissue of broadly 0.005–0.5:1, and preferably 0.05–0.1:1.

The reaction time for achieving complete solubilizing of the collagenous tissue may range from about 30 minutes to 2 hours. The time depends on the quantity of solubilizing agent, specific solubilizing agent used, rate of agitation or stirring, temperature, pH, and degree to which the tissue was initially pulverized or dispersed in the preliminary homogenization treatment.

For the carboxylic acid modifying reaction, the noncollagenous protein contaminate-free, and lipid-free extracted, tissue powder is desirably dried, e.g., in vacuo or by freeze drying, and combined with a carboxylic acid reactive esterifying agent in a nonaqueous organic medium at acidic pH, preferably no more than about pH 3.2, such as about pH 0.1–3.2.

The quantity required should generally satisfy the weight ratio of esterifying agent to dry tissue of broadly 1–30:1, preferably 1–20:1, and more preferably 5–20:1.

In particular, the medium is advantageously a large excess of the esterifying agent in the form of an acidified liquid, such as an acidified alcohol, especially an aliphatic alcohol, such as a water soluble lower alkanol, e.g., methanol and ethanol. The esterification reaction which forms the ester and water is favored by use of an excess of the alcohol to assure efficient formation of the ester product, in the presence of a catalytic amount of an acid such as 0.1 N HCl as acidifying agent, thereby providing a system pH of about 0.1–3.2.

The reaction is desirably effected under anhydrous conditions using dehydrated starting materials for optimum results, although acceptable results are still obtainable with starting materials which have not been dehydrated, such as wet tissue powder.

In general, the esterifying agent may be an aliphatic or aromatic alcohol, such as a lower alkanol or an aryl alcohol (e.g., a phenol or a naphthol), to provide the corresponding aliphatic or aromatic, e.g., alkyl or aryl (e.g., phenyl or naphthyl), ester.

Where the esterifying agent is a solid at room temperature, it may be dissolved in a suitable nonaqueous organic solvent such as acetone, N,N-dimethylformamide (DMF), ethanol, or methyl pyrrolidone, as the organic medium.

The esterification reaction is conducted at the same temperature and for the same reaction time as the acylation reaction, for the same reasons, but since the esterifying agent is advantageously used in large excess as nonaqueous organic reaction medium, the esterifying agent amount will preferably be several times larger than that of the dry starting tissue, e.g. in a weight ratio thereto of about 2–20:1, although the ratio may be 1–30:1, and preferably 1–20:1, in general, especially where the esterifying agent is a solid and an organic solvent is used as the reaction medium.

In the aqueous medium, the completely solubilized material intended for use as the collagenous core, is a transparent, viscous telopeptide-containing collagen "solution" product.

The solubilized product constitutes chemically modified, crosslinkable, telopeptide-containing, naturally crosslinked, collagen, in which the individual helical strands of the triple helix molecules remain in interconnected side by side helical disposition along the corresponding collagen polypeptide backbone, with the terminal amino group-containing site of each given strand still linked to its adjacent non-helical telopeptide end moiety, and with the terminal carboxylic acid group-containing site of the same strand still linked to its adjacent non-helical telopeptide end moiety.

Thus, all three helical strands of one tropocollagen molecule remain linked at their ends to their respective telopeptide moieties, telopeptide moieties may remain crosslinked to adjacent tropocollagen molecules, and adjacent helical strands may remain crosslinked to each other along their central regions, and to telopeptide regions of adjacent tropocollagen molecules, to retain the original polypeptide backbone arrangement and to retain some order of the original intermolecular configuration. However, these strands now contain acylated (succinylated) amino groups which render the collagen soluble at neutral to basic pH, while still preserving the integrity of the intermolecular arrangement.

It will be understood that these individual chemically modified tropocollagen molecules, consequent their solubilization, are no longer in packed staggered arrangement in fibrils of fiber bundles as in the starting tissue, but rather constitute substantially intact separate units, which are completely dissolved in the reaction medium where complete solubilization is carried out. If partial solubilization is carried out, the suspension contains a mixture of intact separate units and various degrees of fiber units sized in dependence upon the extent of solubilization, which are suspended or dispersed in the reaction medium as fine particle material.

Where the tissue powder has already been solubilized in the amine modifying reaction, the recovered and purified acylated product may be dried, e.g., in vacuo or by freeze drying, and then combined with the acidified esterifying agent and reacted to form the corresponding acylated and esterified product. Alternatively, the tissue may first be subjected to the esterification step and the esterified solubilized product is then subjected to the acylation step.

It will be readily apparent to those skilled in the art that in order to provide an implant suitable for example, in the replacement of damaged cornea, the collagenous core must be optically clear and not infiltrated with fibroblasts. In most applications, the collagenous core has a refraction index of preferably from about 1.283 to about 1.545 when the transparent collagenous material is modified with an agent that exhibits an index of refraction in this range. This range can be modified further as necessary, as described next.

For specific ophthalmic applications, it is preferable that the chemical modifying agent be employed that is capable of modifying the collagenous core to provide a solubilized collagen with a high index of refraction. This is most effective for correcting sight. The solubilized collagen is recovered, purified and combined with aqueous liquid to form a telopeptide collagen solution, of a selective index of refraction for correcting sight, as product.

The agent used to achieve such selective index of refraction (nD) is suitably an amine modifying acylating agent which is capable of achieving complete solubilization of the collagen to provide a product that is essentially completely soluble at physiological pH conditions, such as glutaric anhydride, aniline-2-sulfonic acid (nD=1.586), 3-nitrobenzene-sulfonic acid (nD=1.550), 2-formylbenzene-sulfonic acid (nD=1.544), 1,3-benzene-disulfonic acid, 1,2,4,5-benzene-tetracarboxylic acid dianhydride, and B-styrene sulfonyl chloride or like reagents whose particular constituent reactive group or functional group exhibits a high index of refraction or imparts a resultant high index of refraction to the so modified collagenous core substance.

Preferred as a chemical modifying agent to provide a solubilized collagen suitable as the collagenous core of high refractive index in the corneal implant of this invention is B-styrene sulfonyl chloride. Styrene exhibits a refractive index of about 1.545.

Thus, such an agent will generally possess an index of refraction of at least about nD 1.500, such as an index of refraction of from about ND 1.500 to about nD 1.600.

The refractive index of the collagenous core may be modified as well, e.g., reduced, by modifying the collagenous material with an acylating agent such as trifluoroacetic anhydride. Trifluoroacetic acid exhibits a refractive index of about 1.283. The normal cornea provides a refractive index of about 1.370. Common "biologically acceptable" materials exhibit the following nD's: PMMA: about 1.495; and hydrogel intercorneal lenses: about 1.375. It may be possible to combine modified collagen with hydrogel to form a composite lens with varying indices of refraction, all higher than the cornea.

Thus, a biologically acceptable material can be incorporated into the collagenous core (1) of the implant provided by this invention. The "biologically acceptable" material is one that will not impair or diminish the compatibility of acceptance of the implant following transplantation into a suitable recipient. The material is selected from the group consisting of polyhydroxyethylmethacrylate, polymethylmethacrylate, hydrogel, or a combination of any of the foregoing.

Because the collagenous core can be prepared to provide a range of refractive indices, the implant of the present invention will reduce the need for human donor cornea in keratoplasty. By providing such a range of refractive indices, this implant is also useful for correcting refractive errors without the need for corrective devices, e.g., eye glasses and contact lens.

In one embodiment of this invention, the collagenous core (1) of the implant can be derived by chemically modifying pulverized human dermal tissue, using conventional techniques. Such chemical modification can be carried out by contacting the tissue containing the collagen with an acylating or an esterifying agent as described hereinabove.

The periphery (2) of the implant provided by this invention comprises predominantly Type I collagenous material that can be obtained from mammalian tissue, e.g., human tissue or bovine tissue. For purposes of enhancing the non-biodegradability or immunologically-acceptable features of the implant, it is important that the tissue from the Type I collagenous material be autogeneic, i.e., the donor and recipient be the same individual.

In another aspect of this invention, the core (1) and the periphery (2) in the implant are polymerized by means of exposure to polymerizing agents, e.g., ultraviolet irradiation, chemical agents, or a combination of polymerizing agents.

The non-biodegradable corneal implant of this invention can be prepared from the aforementioned collagenous core and periphery materials in a method provided by this invention. This method has two separate polymerizing steps ("two step polymerizing method") and comprises the steps of (a) incubating neutralized fibrous collagen under conditions sufficient to form fibrils; (b) recovering said formed fibrils; (c) contacting said fibrils with a binding agent to bind said fibrils; (d) polymerizing said bound fibrils; (e) replacing a core of said bound fibrils with a soluble collagenous material having acylated amine or esterified carboxyl groups; and (f) polymerizing said soluble collagenous material.

Alternately, the lens may be formed by polymerizing the soluble collagenous core and the fibrous periphery as one unit, i.e., using a single polymerizing step. In this case, the fibrous collagen is placed in the mold to provide a homogeneous layer, the central zone is removed and replaced with soluble collagenous material and the entire unit is polymerized. Thus, the present invention provides an alternative method of forming the non-biodegradable corneal implant described. A prepolymerized implant is formed which comprises a collagenous core having acylated amine or esterified carboxyl groups, and a fibrous collagen periphery, the periphery having been treated under conditions sufficient to form fibrils. The pre-polymerized implant is then polymerized by exposing, e.g., to UV irradiation and/or chemical agents, or both, to form a non-biodegradable corneal implant.

The steps of this method are described in more detail hereinbelow and in the examples which follow.

The fibrous collagen comprises Type I collagen derived from mammalian tissue, e.g., bovine or human tissue. In a preferred aspect of the method, the mammalian tissue comprises autogeneic human tissue.

FF collagen is neutralized (i.e., removing charged particles) by mixing with a buffer solution, e.g., phosphate buffer, at pH 6.0 to about 8.0, preferably from about pH 6.8 to about 7.4.

The neutralized FF collagen is next incubated under conditions sufficient to cause the formation of fibrils. Such conditions comprise a temperature in the range of from about 25° C. to about 40° C., preferably about 37° C., for a period of time of from about 10 to about 45 preferably about 30 minutes or so.

After fibril formation, the fibrils are recovered by conventional recovery techniques, e.g., centrifugation at 12,000 RPM. A fibril pellet is recovered. The recovered pelleted fibril material is then treated by contacting with a binding agent to bind the fibrils. By way of example, suitable binding agents include the above described soluble collagen or collagenous material which has been obtained by treating fibrous Type I collagen with a chemical modifying agent (e.g., an acylating or esterifying agent, or a combination of an acylating and esterifying agent).

Next, the fibril containing collagen mixture is cast upon a suitable support surface, such as a glass or ceramic mold, in order for polymerization or cross-linking to be carried out, e.g., by exposure to ultraviolet irradiation (or gamma irradiation). In order for polymerization or crosslinking to be effectively, the FF collagen must be dispersed prior to polymerizing or crosslinking. This can be done for example, by placing the FF collagen in deionized water. Short wavelength UV light is preferred, such as 7.5 cm from UV source of 8 watts, for about 25 minutes in nitrogen. Polymerization or cross-linking can be also carried out by exposing the molded collagen to chemical polymerizing or cross-linking agents such as isocyanate, aldehyde, e.g., glutaraldehyde, epoxy compounds such as polyglycerol polyglycidyl ether, diglycerol polyglycidyl ether, and such other compounds, or a combination thereof.

From the polymerized fibrous "button" that has been made, a central core zone of suitable area, e.g., 3-4 mm diameter may be excised or cut out by conventional methods, e.g., using a cork bore. The core zone is filled with the soluble collagenous core material, described above, which has acylated amine groups or esterified carboxyl groups or both.

Following replacement of the core zone with such soluble collagenous core material, the entire "button" is exposed to polymerizing or cross-linking steps, e.g., UV irradiation for at least about 20 minutes. Then the "button" is removed from the support surface and allowed to air dry overnight.

After air drying, the button is exposed once again to polymerization or cross-linking conditions. The polymerization or cross-linking of the collagenous core and the fibrous collagen containing periphery is important to provide a corneal implant that is non-biodegradable so as to resist breakdown following transplantation.

Alternately, the entire unit may be polymerized as "one". It has also been found desirable to melt the central core or soluble collagenous core at about 35°-38° C. before air drying and subsequent crosslinking. In addition, melting the soluble, binding collagen, in the fibrous component before crosslinking has been found to improve the strength and elasticity of the implant.

Accordingly, the prevent invention provides a method of forming the aforesaid non-biodegradable corneal implant comprising the steps of forming a pre-polymerized implant comprising a collagenous core having acylated amine or esterified carboxyl groups, and a fibrous collagen periphery, the periphery having been treated under conditions sufficient to form bound fibrils; and polymerizing said collagenous core and said bound fibrils to form the non-biodegradable corneal implant.

The corneal implant thus prepared can be stored for long periods of time, up to 6 months or even longer in saline solution (0.2M).

Those skilled in the art will appreciate that the corneal implant of the present invention can be used in various ophthalmic applications. One particularly useful application is as an autoimplant for correcting sight in which the implant is formed into a mass of selective shape and size corresponding to an effective implant device. The implant may be so formed from a mold having a concave surface of selective size and shape corresponding to an effective shape and size for the outer surface of the damaged cornea to be replaced or reshaped. Other uses of the corneal implant described herein include corneal onlay, corneal inlay and intraorbital lens (e.g., behind the iris). Onlay lends will be placed on the surface of the existing cornea, after removal of epithelial cells which should migrate over the lens. Inlay lens will be placed in the corneal lamellae and should not retard diffusion of oxygen and nutrients. Glutaric lens, hydrated, contain approximately 85-90% water.

Again, it is preferable to melt the soluble, central core collagen prior to drying and subsequent polymerization. It has also been recently discovered that a strong oxidizer, such as sodium persulfate, available from Aldrich Chemical Company, Milwaukee, Wisconsin, will dramatically accelerate the polymerization reaction using UV-irradiation, even in the presence of oxygen. This is particularly evident if the soluble collagen contains some methacrylic moieties. Other suitable oxidizing agents include sodium bisulfite, ferrous chloride tetrahydrate, sodium thiosulfate, all available from Aldrich Chemical Company, Milwaukee, Wisconsin.

Figure 1A:
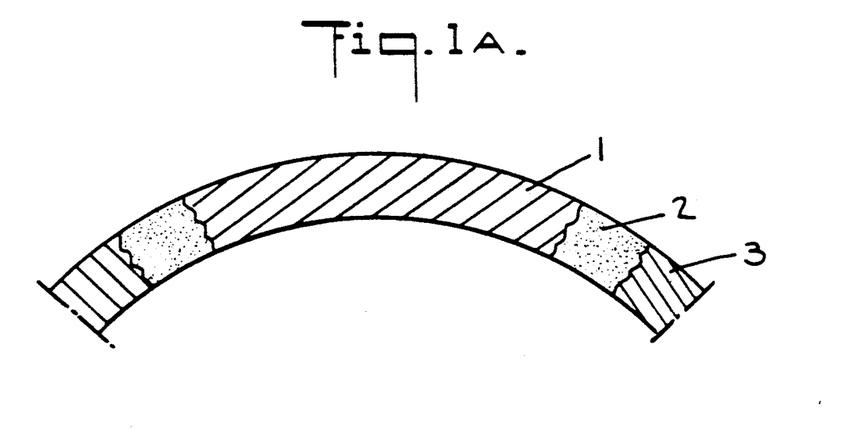
Figure 1B:
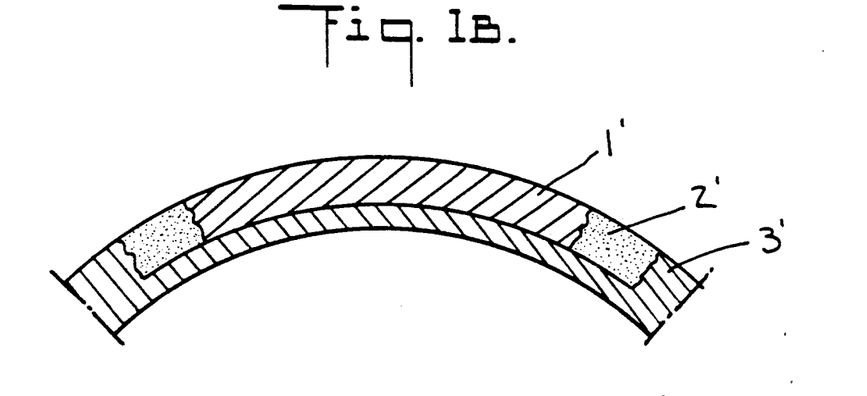
Figure 1C:
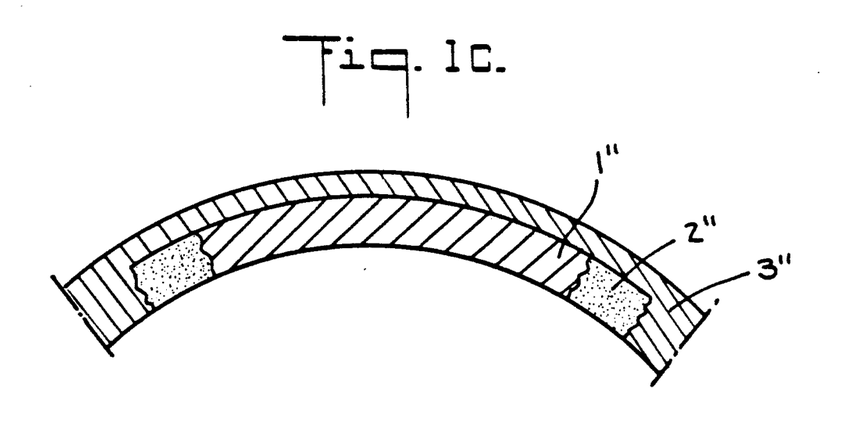
Figures 2A, 2A:
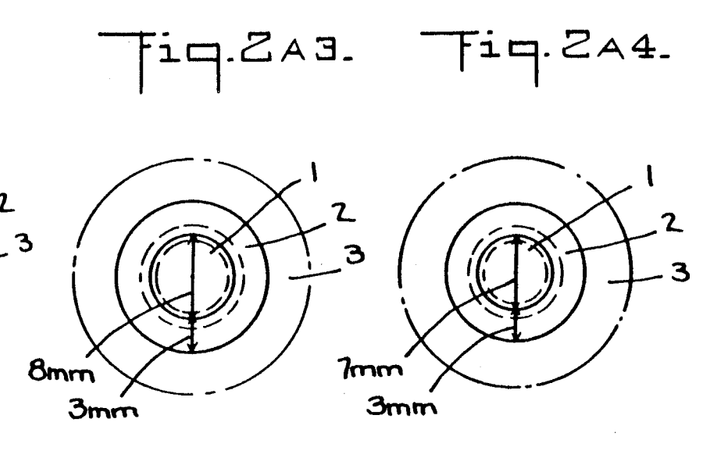
Figures 2A, 2A:
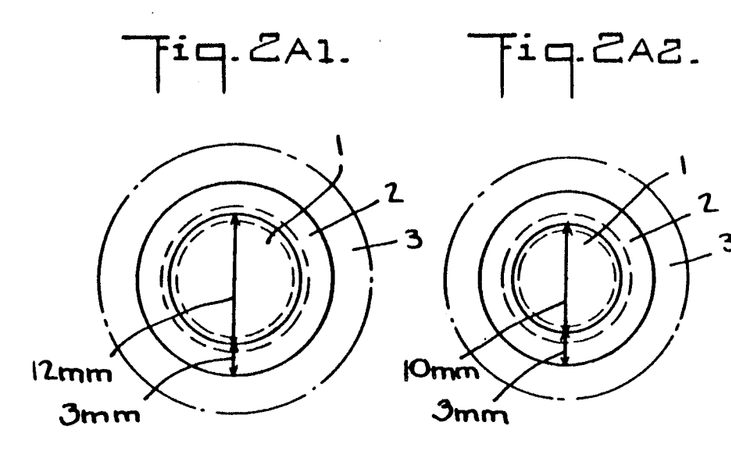
Figures 2B, 2B:
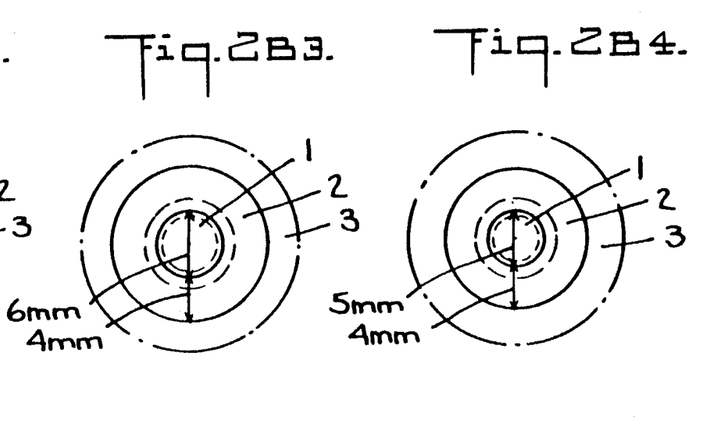
Figures 2B, 2B:
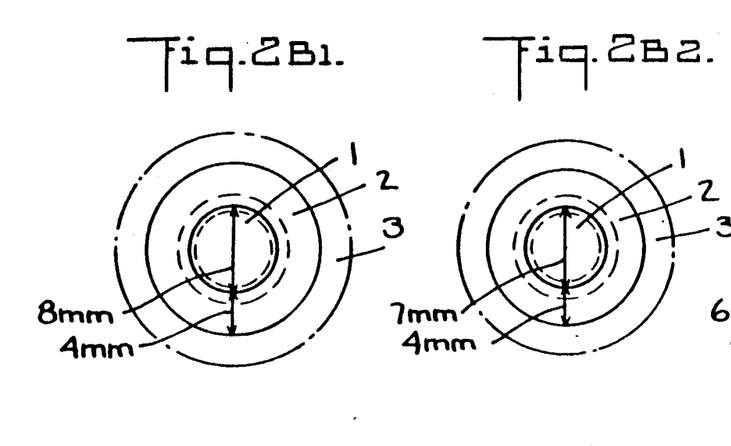

Referring to FIG. 1, three embodiments of the two phase corneal implant of the present invention. In 1A, there is shown a full thickness corneal graft comprising (1) a clear central zone; (2) a collagen fiber periphery; and (3) the surrounding corneal tissue. FIG. 1B and 1C are illustrations of partial thickness corneal implants. 1B is an on-lay lens and 1C is an intrastromal lens.

It is preferable that the lenses be grafted or implanted so that the fibrous periphery is attached, i.e. sutured, to the scleral tissue, i.e. at the limbus.

FIG. 2 are front view illustrations of the two phase corneal implant of the present invention within various dimensions that are not to be construed as limiting. The total diameter of the implant can be from about 6 mm to about 20 mm. The thickness of the fibrous periphery can range from about 2 mm to about 6 mm. The diameter of the clear optical core can be from about 2 mm to about 8 mm. The implant thickness can vary from about 0.025 mm to about 2.0 mm. The curvature of the concave can also vary as follows: top diameter from about 6 mm to about 20 mm; bottom diameter from about 3 mm to about 12 mm.

EXAMPLES

The following examples are set forth by way of illustration and not limitation of the present invention.

Example 1: Preparation of Two Phase and Corneal Implant from Bovine Tissue

A. Fibrous Type I collagen was prepared from bovine material (calf hide) using the following procedure:
1. Clean, dehaired split hides, which are commercially available from the Andre Manufacturing Co., Newark, New Jersey, and store frozen in sealed plastic bags until ready for use.
2. Thaw approximately 200g of cow hide at room temperature.

3. Cut the hide into small pieces, approximately 1 cm³ using a scalpel and tweezers. Weigh the wet tissue and record its weight.
4. Place the cow hide in 15 liters of 0.5M acetic acid and stir at room temperature using a lightning mixer for at least one hour. The cow hide will swell.
5. Add 2% or 3.9g of pepsin from porcine stomach mucosa (manufactured by Sigma Chemicals, St. Louis, Missouri) to the cow hide solution, after dissolving it in approximately 10 mls of 0.5M acetic acid. Continue stirring with mixer overnight.
6. Add 1% or 1.96g of the above pepsin to the cow hide solution dissolved in approximately 10 mls of 0.5M acetic acid. Continue stirring with mixer overnight.
7. Refrigerate the dissolved cow hide solution until it is uniformly at a temperature of about 4° C. This may take until overnight.
8. Remove the solution from the cooler and begin stirring with the lightning mixer. Increase the pH of the solution to 9.0 using 10N NaOH to denature the pepsin. Ice cubes may be added during the process to keep the solution cold. (Collagen will precipitate at pH 9.0 if the temperature is higher than 6° C.) Quickly return the solution to 4° C. The solution must remain in the cooler for at least 4 hours.
9. Remove the solution from the cooler and centrifuge at 4° C. for 30 minutes at 9 rpm. Save the supernatant, which contains the collagen and discard the precipitate which contains the pepsin.
10. Add NaCl to the solution to bring up the concentration to 2.5M. This will precipitate the desired collagen. Stir with the lightning mixer for at least two hours.
11. Centrifuge for 30 minutes at 9 rpm to recover precipitate. The resultant collagen precipitate is collected and then reconstituted in 15liters of 0.5M acetic acid (at least two hours).
12. The collagen solution is precipitated again by adding enough NaCl to the solution to bring up the concentration to 0.8M. It is stirred well for at least two hours then centrifuged for 30 minutes at 9 rpm.
13. The precipitate is collected and then reconstituted in 15 liters of 0.5M acetic acid (at least two hours).
14. Enough NaCl is added to the collagen solution to bring up the concentration to 0.8M. The precipitate is formed by mixing for at least two hours. Centrifugation at 9 rpm for 30 minutes will recover the precipitate.
15. For the final time the precipitate is collected and then reconstituted in 0.1M acetic acid to provide a high purity of approximately 0.3 percent wt/wt collagen Type I solution having a pH of about 3.
16. The collagen solution is filtered first through a prefilter which has a pore size of about 0.3 um and then through a final filter which has a pore size of 0.22 um for sterilization. This material can now be used in the modification procedure or for preparation of fibrils.

Bovine Type I collagen is soluble in organic acid and undergoes fibril formation under physiological conditions, e.g., neutral pH, body temperature, in buffer. The periphery of the two part implant was composed of this bovine fibril-forming (FF) collagen. Bovine physiological soluble (PS-collagen) was prepared by chemically acylating acid solutions of bovine FF-collagen. The bovine FF-collagen was treated with a monofunctional acylating agent, such as glutaric anhydride. The glutaric treated collagen was clear and viscous in buffer at pH 6.8. The central zone was composed of this PS-collagen.

The corneal implant was made as follows: The bovine FF-collagen formed above was mixed with phosphate buffer at pH 6.8 to neutralize the preparation. This was incubated at 37° C. for 30 minutes to allow fibril formation to occur. The fibrils were recovered by centrifugation at 12,000 RPM. The fibril pellet was recovered and mixed with approximately 0.1 ml of PS-collagen to bind the material. The mixture was then cast onto a concave microscope slide of about 14 mm in diameter and dispersed in deionized water. This fibrous collagen material was cross-linked by exposure to short wavelength UV light (7.5 cm from source of 8 watts) for 25 minutes, in nitrogen. The polymerized fibrous button was trimmed and a central zone of 9 mm was cut at with a cork bore. This zone was then filled with PS-collagen and the button was again exposed to UV irradiation for 20 minutes. The button was removed and allowed to air dry overnight. The dried button was then exposed to UV irradiation once again. The button was then stored in 0.2M saline solution. The button had a clear central zone and a white, fibrous periphery, as shown in FIG. 1.

EXAMPLE 2: PREPARATION OF TWO PHASE CORNEAL IMPLANT FROM HUMAN TISSUE

Human skin biopsy tissue (or human skin tissue obtained from reconstructive surgery, or the like), of the donor patient, is immediately frozen. Specimens of the frozen tissue are dissected to remove the attendant epidermal and subcutaneous layers, and the remaining dermal layer is sectioned.

The following steps and procedures are carried out.

STEP 1 —Dissection

1) Remove skin sample from the freezer and equilibrate at room temperature for no more than four hours.
2) Place the skin on a clean, dry cutting board. Only one specimen can be dissected on a cutting board at any given time. The dermal layer of the skin is dissected using a scalpel with a fresh blade, tweezers, and scissors that have been soaked in alcohol. The epidermal layer of the skin and any hair on the skin is removed by scraping the outer portion of the skin with the scalpel while holding the skin in place with the tweezers. The inner portion of the skin, which may contain a lot of fat can be cut off with scissors and then scraped with the scalpel until the white dermal layer remains.
3) The wet dermis is then cut into very small pieces with scissors and placed into a pre-weighed labelled sterile 50ml centrifuge tube. The weight of the centrifuge tube is subtracted from the weight of the centrifuge tube and dermis. The weight of the dermis is then recorded.

STEP 2 —Purification and Sterilization

4) Add to the dermis 10 mls of sterile filtered 0.1N HCl. Cap the centrifuge tube and place it on a shaker for two hours.
5) Centrifuge the tube for 15 minutes at 8 revolutions per minute. Using a sterile transfer pipet, remove the supernatant which is the excess HCl being careful not to remove any dermis.

6) To the dermis add 10 mls of reagent alcohol (formula 3A—denatured). Cap the centrifuge tube and place on a shaker for two hours.
7) The tube is then centrifuged for 15 minutes at 8,000 rpms. Following centrifugation, the tube is sprayed down with alcohol and placed in the sterile hood.
NOTE: From this point on the specimens are to be processed using aseptic techniques in the sterile laminar flow hood.
8) Using a sterile transfer pipet the alcohol/supernatant is removed and discarded. Fifteen mls of sterile water is added to the dermis. The tube is capped and shaken well. The centrifuge tube is removed from the hood and centrifuged for 15 minutes at 8 rpm. The tube is sprayed with alcohol and returned to the sterile hood.
9) The dermis is washed two more times with sterile water, repeating step 9. On the last wash after the water is removed add 10 mls of sterile filtered 0.5M Tris Buffer. The dermis pieces will be equilibrated for one hour. Check the pH of the solution, it should be between 8.5 and 9.0. If it is not then adjust with sterile filtered 1N HCl or 1N NaOH.

STEP 3 —Modification of the Collagen

10) The sample is placed in the small mixer attachment of the Waring blender. An aliquot of 1 part glutaric anhydride per 10 parts of dermis wet weight in 1 ml of DMF is added to the solution. The top is placed on the blender and blending begins. After approximately seven minutes into the blending, a second aliquot of glutaric anhydride and DMF exactly similar to the first one will be added. Each sample will receive 5 - 1 minute blendings over a period of 15 minutes. The blender should not be allowed to build up heat because heat will break down the collagen.
11) After blending, the pH should be between 6.8 and 7.4. If it is not then sterile filtered 1N HCl can be added to make this adjustment.
12) The sample is removed from the hood and centrifuged at 8 rpm for 30 minutes. The tube is sprayed down with 70% alcohol and then returned to the hood.
13) The supernatant is removed with a sterile transfer pipet and then discarded. The layer on top of the residue (disperse fraction) is scraped off using a sterile spatula and placed into a labelled 15 ml sterile centrifuge tube.
14) The disperse fraction is washed three times with sterile water similar to the procedure in step 9.
15) The disperse fraction is redispersed in sterile phosphate buffered saline. Fibers will form.

The above procedures yielded fibrous collagen.

Preparation of soluble collagen from human dermis was carried out as follows:

Processed dermis is incubated in pH 9.0 buffer for at least 2 hours. This is then homogenized in a small container using a commercial Waring blender. To the homogenate is added the amine reactive modifying agent, preferable glutaric anhydride, at about 1 part to 10 parts of wet tissue. This mixture is blended about 5 times for one minute each. Care is taken to avoid reaching an excessive temperature during the blending. A second aliquot of amine reactive modifying agent is added and the mixture is blended 5 more times. The pH of the mixture is then decreased to 6.7-7.4 using 1N hydrochloric acid and the mixture centrifuged at about 8,000 rpm for 20 minutes. The soluble collagenous component appears as a gelatinous mass covering the dispersed tissue. This is removed and placed in alcohol. The material immediately precipitates and is washed 3 times in alcohol. At this point it is preferable to dry the alcohol precipitate in a laminar flow hood. The dried precipitate is then dissolved in buffer at pH 6.8-7.4 to a viscous consistency of approximately 40,000 centipoise. This solution can then used as the clear core for the human two phase corneal implant.

An alternate method has been found to obtain additional soluble collagen. This alternate method involves taking the supernatant from the above mentioned centrifugation. This solution is adjusted to pH 4.3 and stirred for about 1 hour. The solution is then adjusted to pH 6.8-7.4. After about 10 minutes, clear, gelatinous material forms in the solution. This material appears to be solubilized dermal collagenous material which can also be used for the clear core of the human two phase corneal implant. This material may be placed in alcohol (e.g., ethanol) for storage.

In the case of all human material, skin specimen can be processed as described in the aforementioned U.S. Pat. No. 4,969,912 and European Patent Application Publication No. 330,389. Using these procedures, human physiologically soluble (PS) collagen was prepared as was human fibril-forming (FF) collagen dispersions. Unlike the bovine FF-collagen, the human FF-collagenous fraction is not soluble in organic acids. Instead, human FF-collagen is dispersed, by chemical treatment, into a form that will undergo rapid fibril organization when mixed with physiological fluid. An aliquot of human FF-collagen was mixed with a drop of human PS collagen. This mixture was placed onto a concave microscope slide as described above. It is important that the human FF-collagen be dispersed in deionized water. The material was irradiated with UV, after which a central zone of about 4-8 mm was removed and then filled with human PS-collagen., The button was again exposed to UV irradiation. The button was removed and mix dried and again exposed to UV irradiation. The final product button had a slightly opaque periphery and a clear central core. When immersed in 0.2m saline solution, the periphery immediately became white and opaque and the center remained clear.

Two phase corneal implants were prepared using fibrous collagenous material prepared from human dermis and soluble collagen obtained from bovine collagen. Since the cornea is avascular, such an implant is efficacious as a full thickness corneal graft. It should be noted that previous attempts with collagen corneal implants (Type IV in particular) have failed due to degeneration at the periphery of the implants. The two phase implant, even with a bovine collagen core, may be more stable because the periphery is fibrous and composed of autologous collagenous material.

In Example 3 which follows, the in vivo efficacy of the corneal implant of the present invention was evaluated in one animal model.

EXAMPLE 3: IN VIVO EFFICACY OF THE CORNEAL IMPLANT IN RABBIT MODEL

Two corneal grafts were prepared from rabbit skin. Rabbit skin was dissected to remove fur, epidermal layer, and underlying subcutaneous tissue. Sections of resulting dermal layer were minced, weighed and placed in 70% alcohol for 16-18 hours. The tissue was removed from the alcohol and treated with 0.1N hydrochloric acid for 2 hours. The tissue was recovered following centrifugation at 8,000 rpm for 30 minutes, washed with sterile water and placed in 10 volumes of 0.5M Tris buffer at pH 8.7. After equilibration for 2 hours, the tissue was placed in the small blender container (12–37 ml) and blended using a Commercial Waring blender. The tissue was homogenized 2 times for about 1 minute each time. At this point the tissue pieces were still intact. The tissue was dispersed by adding 1 part of glutaric anhydride per 10 parts of wet dermis. The anhydride was dissolved in 0.2–1.0 ml of dimethyl formamide (DMF). The mixture was blended 4 times for about 1 minute each time. After 1 minute of continuous blending, the temperature of the blender container began to increase and the homogenization was stopped until the container cooled. A second aliquot of glutaric anhydride was added and the mixture blended 4 times more, as described above.

The pP of the mixture was adjusted to 6.8–7.4 by addition of 1.0N sodium hydroxide or hydrochloric acid. The mixture was then centrifuged at 8,000 rpm for 30 minutes to separate the dispersed fractions. The supernatant was removed and stored at 4° C. The gelatinous fraction was removed and placed in 70% alcohol and the dispersed fraction removed and washed three times with sterile water.

Rabbit corneal grafts were formed as follows:

Graft 1. The dispersed fraction, in sterile water, was mixed in sterile phosphate buffered saline, pH 7.3, to form fibers. The fibers were recovered by centrifugation and mixed with a small aliquot of glutaric modified, soluble bovine collagen. The mixture was then placed in a glass mold 15 mm in diameter and 2 mm in depth. A thin layer was applied to a diameter of approximately 12 mm and the material exposed to ultraviolet radiation (254 nm) for 20 minutes in a nitrogen atmosphere. The polymerized fibrous disc was removed and a center core of about 5 mm removed. The center was filled with an aliquot of glutaric modified, soluble, bovine collagen and again subjected to UV irradiation. The final graft appeared as a 12 mm concave disc with a 5 mm clear central core. This was placed in a clear pouch, sealed and gamma sterilized.

Graft 2. The fibrous portion was prepared as described above. The soluble fraction was again composed of glutaric modified, soluble, bovine collagen. Soluble fractions of glutaric modified, rabbit collagen were available and made into two-phase corneal grafts, but were not implanted. The graft was made in one step. Fibers were isolated as discussed above, mixed with a small aliquot of soluble collagen and placed in a concave glass mold, 22 mm in diameter and 5 mm in depth. A center core of about 5 mm was removed and filled with glutaric modified, soluble, bovine collagen. The mixture with clear center and fibrous periphery was placed in an oven at 38° C. for 3 minutes to "melt" the soluble fraction. The mold was then placed in a sterile, laminar-flow hood to dry the graft. After about 4 hours, the mold was removed from the hood and subjected to UV-irradiation, in nitrogen, for 20 minutes. The implant was trimmed to about 12 mm diameter and contained a 5 mm clear center core. It was placed in 70% alcohol, washed with sterile water, and placed in a sterile pouch for storage.

The first graft was used as a full thickness corneal graft in the rabbit model. The rabbit was anesthetized and a 7 mm trephine was used to remove a core of the natural cornea. The graft was trephined to 7 mm and sutured into the rabbit eye. The graft appeared clear but was difficult to suture. At one point, the sutures tore through the graft. The eye was treated with antibiotics and closed using sutures. The rabbit remained alive for about 24 hours at which time the grafted eye was enucleated and prepared for histopathological examination. Results indicated the beginning of healing at the margin between the graft and the host tissue. A few inflammatory cells were present near the wound margin and there was a hint of reepithelialization. The graft seemed to be well tolerated and on its way towards proper healing.

The second graft was also used as a full thickness corneal graft in the rabbit model. The graft was sutured into the rabbit eye as discussed above. In this case, the graft sutured extremely well. The fibrous periphery exhibited unexpected strength and flexibility. After implantation, the central core was clear. Slit-lamp examination of the graft indicated excellent approximation to the host tissue. There was no adverse tissue reaction and the graft remained intact. There was, however, clouding of the central core and upon enucleation, at approximately 4 weeks, minute erosion at the apex of the graft. The enucleated eye was again prepared for histopathological evaluation.

What is claimed is:

1. A non-biodegradable corneal implant comprising:
   (1) a polymerized transparent, solubilized, non-fibrous collagenous core having acylated amine or esterified carboxyl groups, and
   (2) a polymerized periphery surrounding said core, said periphery comprising fibrous collagen in the form of fibrils under suitable physiological conditions.

2. The implant according to claim 1 wherein said (1) core is derived from a member selected from the group consisting of purified Type I collagen, purified Type IV collagen, predominantly Type I collagenous material obtained from human tissue, or combinations of any of the foregoing.

3. The implant according to claim 2 wherein said (1) core comprises predominantly Type I collagenous material obtained from human tissue.

4. The implant according to claim 3 wherein said Type I collagenous material comprises fibril forming collagen.

5. The implant according to claim 1 wherein said (1) core comprises transparent collagenous material modified with an agent that exhibits an index of refraction from about 1.283 to about 1.545.

6. The implant according to claim 1 wherein said (1) core optionally further comprises a biologically acceptable material selected from the group consisting of polyhydroxyethylmethacrylate, polymethylmethacrylate, hydrogel, or a combination of any of the foregoing.

7. The implant according to claim 1 wherein said (2) periphery said fibrous collagen comprises predominantly Type I collagenous material.

8. The implant according to claim 7 wherein said Type I collagenous material is obtained from human tissue or bovine tissue.

9. The implant according to claim 8 wherein said Type I collagenous material comprises autogeneic human tissue.

10. The implant according to claim 7 wherein said (1) collagenous core has been derived by chemical modification of pulverized human dermal tissue.

11. The implant according to claim 7 wherein said (1) collagenous core has been derived by chemical modification of soluble collagen extracted from mammalian tissue.

12. The implant according to claim 10 wherein said chemical modification has been carried out by contacting with an acylating agent or an esterifying agent.

13. The implant according to claim 11 wherein said chemical modification has been carried out by contacting with an acylating agent or an esterifying agent.

14. The implant according to claim 1 wherein said (1) core and said (2) periphery have been polymerized by exposure to a member selected from ultraviolet irradiation, chemical agent or a combination thereof.

15. A method of making the non-biodegradable corneal implant of claim 1, said method comprising the steps of:
   (a) incubating neutralized fibrous collagen under conditions sufficient to form fibrils;
   (b) recovering said formed fibrils;
   (c) contacting said fibrils with a binding agent to bind said fibrils;
   (d) polymerizing said bound fibrils;
   (e) replacing a core of said bound fibrils with a soluble collagen having acylated amine or esterified carboxyl groups; and
   (f) polymerizing said soluble collagen.

16. The method according to claim 15 wherein the step of incubating (a), said fibrous collagen has been neutralized by treating with a buffer at a pH in the range of from about 6.8 to about 7.4.

17. The method according to claim 15 wherein the step of incubating (a), said fibrous collagen comprises Type I collagen derived from mammalian tissue.

18. The method according to claim 17 wherein said mammalian tissue comprises autogenic human tissue.

19. The method according to claim 15 wherein step (c) said binding agent is a member selected from the group consisting of soluble collagenous material having acylated amine, esterified carboxyl groups or a combination of any of the foregoing.

20. The method according to claim 15 wherein said soluble collagen having acylated amine or esterified carboxyl groups is selected from purified Type I collagen, purified Type IV collagen, predominantly Type I collagenous preparations or a combination thereof.

21. The method according to claim 20 wherein said soluble core collagen comprises chemically modified solubilized, predominantly Type I collagenous material.

22. The method according to claim 21 wherein said chemical modification has been carried out by contacting with an acylating agent or an esterifying agent.

23. The method according to claim 15 wherein said polymerizing steps (d) and (e) comprise air drying followed by exposure to ultraviolet radiation or to chemical agents.

24. The method according to claim 15 wherein before the step (f) of polymerizing said soluble collagen, said bond fibrils and said core collagenous component are melted and dried.

25. The method according to claim 15 wherein (f) polymerizing is carried out in the presence of an oxidizing agent.

26. The method according to claim 25 wherein said oxidizing agent comprises a member of the group consisting of sodium persulfate, sodium thiosulfate, ferrous chloride tetrahydrate, sodium bisulfite, or a combination of any of the foregoing.

27. A method of forming the non-biodegradable corneal implant of claim 1, said method comprising the steps of:
   forming a pre-polymerized implant comprising a collagenous core having acylated amine or esterified carboxyl groups, and a fibrous collagen periphery, said periphery having been treated under conditions sufficient to form bound fibrils; and
   polymerizing said collagenous core and said bound fibrils to form the non-biodegradable corneal implant.

* * * * *